United States Patent [19]

Newman

[11] Patent Number: 4,769,121

[45] Date of Patent: Sep. 6, 1988

[54] SINTERED PELLET WITH BIOCHEMICALLY ACTIVE LAYER

[75] Inventor: Arnold L. Newman, Kensington, Md.

[73] Assignee: Biotronic Systems Corporation, Rockville, Md.

[21] Appl. No.: 44,769

[22] Filed: May 1, 1987

[51] Int. Cl.[4] .................... A01G 5/06; G01N 27/26; B05D 5/12; A01N 1/00
[52] U.S. Cl. .................................... 204/403; 427/4; 427/10; 427/58
[58] Field of Search ............................ 427/10, 58, 4; 29/25.41; 361/271; 422/69; 204/403

[56] References Cited

U.S. PATENT DOCUMENTS

| | | | |
|---|---|---|---|
| 4,072,576 | 2/1978 | Arwin | 435/7 |
| 4,236,893 | 12/1980 | Rice | 422/69 |
| 4,434,236 | 2/1984 | Freytag | 436/541 |
| 4,453,126 | 6/1984 | Volgyesi . | |
| 4,571,543 | 2/1986 | Raymond et al. . | |
| 4,592,894 | 6/1986 | Panitz | 422/69 |
| 4,615,983 | 10/1986 | Koyama | 422/69 |

OTHER PUBLICATIONS

Rodney R. Walters, "Affinity Chromatography", Analytical Chemistry, vol. 57, No. 11, Sep. 1985, pp. 1099A–1114A.
Sintered-Anode Tantalum Capacitors by Sprague Electric Co.
Molecular Design for Electroanalysis, by Murray et al., Analytical Chemistry, vol. 59, No. 5, Mar. 1, 1987.
Kinetics of Electron–Transfer Cross–Reactions within Redox Polymers . . . , by Anson et al., Journal of the American Chemical Society, vol. 105, No. 15, 1983, p. 4884.
New Model for the Interior of Polyelectrolyte Coatings on Electrode Surfaces . . . , by Anson et al., Journal of the American Chemical Society, vol. 105, No. 5, 1983, p. 1096.
"Affinity Chromotography", by I. Parikh et al., Aug. 26, 1985, Chemical and Engineering News, pp. 17–32.
"Adsorption of Blood Proteins on Metals Using Capacitance Techniques", by Stoner et al., The Journal of Physical Chemistry, vol. 74, No. 5, Mar. 5, 1970.

*Primary Examiner*—Shrive P. Beck
*Assistant Examiner*—Vi Duong Dang
*Attorney, Agent, or Firm*—Indyk, Pojunas & Brady

[57] ABSTRACT

A sintered powder electrode has a biochemically active layer embedded in pores of the electrode. Molecules bind to or are displaced from the biochemically active layer, which drastically changes electrical properties of the electrode. The electrode can be used in an affinity chromatography column or in a capacitive affinity sensor.

13 Claims, 2 Drawing Sheets

SINTERED PELLET WITH BIOCHEMICALLY ACTIVE LAYER

BACKGROUND OF THE INVENTION

Cross-reference is made to two U.S. patent applications; Ser. No. 044767, for Added Array Of Molecular Chains For Interfering With Electric Fields, by W. D. Stanbro et al.; and Ser. No. 044761, for Three Dimensional Binding Site Array For Interfering With An Electrical Field, by W. D. Stanbro, which were filed the same date and were assigned to the same entity as this application.

The invention relates to a means for generating an electrical field having a means for interfering with that field. More specifically, the invention relates to an electrode with a porous body having an embedded biochemically active layer.

Electrodes with porous bodies are known. Sintered-anode capacitors in glass-to-tantalum cases are available from the Sprague Co., for instance. Tantalum powder is pressed and heated to produce a sintered porous body. A tantalum wire is embedded as an electrical lead that extends from the body. An amorphous $Ta_2O_5$ film is produced electrolytically to electrically insulate and passivate the tantalum. This forms one electrode and a dielectric film of a capacitor which is covered by a glass-to-tantalum case.

In composition analysis, capacitive sensors have been used to determine the concentration of a specific gas in a mixture, or an analyte in a fluid, for example. Such sensors measure a capacitance that changes with the concentration.

Capacitive affinity sensors measure the concentration of an analyte by detecting a change in capacitance as an analyte molecule moves in or out of an electric field between two electrodes of the sensor, for instance. The moving analyte molecule has a low dielectric constant and displaces solvent molecules having higher dielectric constants from a biochemically active layer between the two electrodes. The displacement of the solvent molecules by the analyte molecules reduces capacitance between the two electrodes. The capacitance between the two electrodes is inversely proportional to the concentration of the analyte being measured by such a sensor.

Applicant has developed a capacitor for determining the concentration of an analyte in a fluid, for instance. Biospecific binding reactions occur in a space between electrodes of a capacitive sensor. These reactions occur among molecules of a binding agent immobilized on a surface and an analyte in a fluid. These reactions result in the displacement of small fluid molecules having high dielectric constants by large biochemical molecules having low dielectric constants. This displacement of molecules changes the dielectric constant of the capacitor.

Raymond et al. U.S. Pat. No. 4,571,543 discusses a capacitor for detecting and measuring the concentration of specific nonaqueous materials or constituents in fluids. The capacitor is layered with a coating of silane and then a coating of certain polymers. These polymers form membranes that are permeable to constituents of the fluids. The constituents penetrate through the membrane to change the dielectric constant of a solution under the membrane.

Volgyesi U.S. Pat. No. 4,453,126 concerns a capacitor for monitoring the concentration of anaesthetic gas in a breathing mixture. The capacitor has a dielectric of lipids or elastomers which permit the absorption of the anaesthetic gas to vary electrical characteristics of the sensor.

"Adsorption Of Blood Proteins On Metals Using Capacitance Techniques", by Stoner et al., The Journal of Physical Chemistry, Vol. 74, No. 5, March 5, 1970, describes a differential capacity method for measuring adsorption of proteins on solid metal electrodes.

Arwin et al. U.S. Pat. No. 4,072,576 relates to a capacitive method for studying enzymatic activity and for studying an immunological reaction. An adsorbed polypeptide substrate is used to study enzymatic activity and an antigen is adsorbed onto an electrode surface to study the reaction of the antigen with an antibody.

Molecular Design for Electroanalysis, by Murray et al., Analytical Chemistry, Vol. 59, No. 5, March 1, 1987, discusses chemically modified electrodes for use in sample analysis, and the use of electroactive polymer films, like poly-L-lysine, on such electrodes. These films facilitate oxidation-reduction reactions at the electrodes.

Kinetics of Electron-Transfer Cross-Reactions within Redox Polymers; Coatings of a Protonated Polylysine Copolymer with Incorporated Electroactive Anions, by Anson et al., Journal of the American Chemical Society, Vol. 105, No. 15, 1983, p. 4884, describes electrodes coated with polymer layers that form a three dimensional arrangement of catalytic sites. These layers comprise a random orientation of polymer coils to facilitate oxidationreduction reactions at the electrode. New Model for the Interior of Polyelectrolyte Coatings on Electrode Surfaces; Mechanisms of Charge Transport through Protonated Poly(L-lysine) Films Containing $Fe^{III}(edta)^-$ and $Fe^{II}(edta)^{2-}$ as Counterions, by Anson et al., Journal of the American Chemical Society, Vol. 105, No. 5, 1983, p. 1096, also describes such electrodes.

In composition analysis, affinity chromatography has been used to determine the presence or concentration of an analyte in a fluid. The analyte is chemically separated or isolated from the fluid, as described in two articles entitled "Affinity Chromatography", one by I. Parikh et al., Aug. 26, 1985, Chemical and Engineering News, pp. 17–32 and the other by R. Walters, September, 1985, Analytical Chemistry, Volume 57, No. 11, pp. 1099A–1114A.

None of the above patents or articles concern a porous electrode having a biochemically active layer embedded in pores of the electrode.

SUMMARY OF THE INVENTION

The invention concerns an electrode having a body with pores that interconnect and a biochemically active layer that is embedded in the pores of the body. In a preferred version of the invention, analyte molecules bind to or are displaced from the biochemically active layer to drastically affect the electrical properties of that electrode.

The invention can be used as an electrode and dielectric material of a capacitive affinity sensor or as an electrode of a column for an affinity chromotography device, for instance.

DETAIL DESCRIPTION

Figure 1:
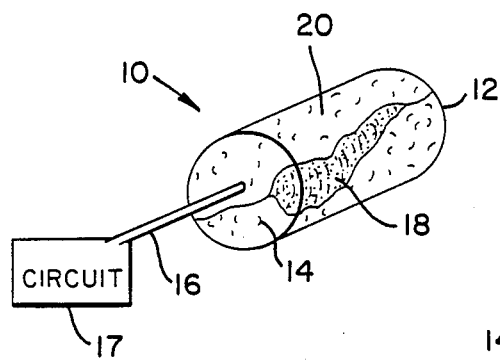
FIG. 1 shows an electrode according to this invention.

FIG. 1 shows an electrode according to this invention. Though shown as a cylinder, the electrode 10 can have many shapes. The electrode 10 may be flat and rectangular or round like a disk, for instance. The electrode 10 has a porous body 12. The body 12 has pores 14 that interconnect to form a passage for fluids through the body 12.

In a preferred version, the body 12 comprises sintered tantalum. A body of sintered tantalum readily wicks fluids into the pores 14 of the body 12, filters fluid, and provides a large, tortuous surface in a small volume. This surface has many binding sites for analyte molecules in a fluid, for instance. Such molecules are more likely to contact and, thus, bind to a tortuous surface than a planar surface.

Other powdered metals can be sintered and formed into an electrode 10 of FIG. 1, for instance. Such powdered metals are discussed in the *Metals Handbook Ninth Edition*, Vol. 7, Powder Metallurgy, published by the American Society for Metals, Metals Park, Ohio. Ceramics, glass and semi-conductors can also be sintered.

A lead 16 is embedded into the body 12 to extend as a point of electrical connection to an electrical circuit 17. This circuit 17 applies a voltage to the electrode 10 and determines changes in electrical properties of the electrode 10, as explained below.

The body 12 has a passivating layer 18 over the entire surface area of the body 12. The passivating layer 18 not only covers the external surface of the body 12, but covers all surfaces within the body 12 of the interconnected pores 14. Only a portion of the passivating layer 18 is shown. The passivating layer 18 comprises a film of electrolytically formed $Ta_2O_5$.

A biochemically active layer 20 is embedded into the body 12 over the entire passivating layer 18. The biochemically active layer 20 is embedded to not only cover the passivating layer 18 on the external surface of the body 12, but to cover the passivating layer 18 on all the surfaces within the body 12 of the interconnected pores 14. Only a portion of the biochemically active layer 20 is shown.

As explained below, a fluid containing analyte molecules is introduced into pores 14 of the electrode 10. Such analyte molecules are biospecific to the biochemically active layer 20. The analyte molecules bind to or displace other molecules from the biochemically active layer 20, which affects electrical properties of the electrode 10.

The circuit 17 determines any change in electrical properties of the electrode 10. The circuit 17 then accesses a look-up table stored in a memory of the circuit 17 to relate a change in electrical properties to a concentration of analyte molecules in the fluid, for instance.

Figure 2:
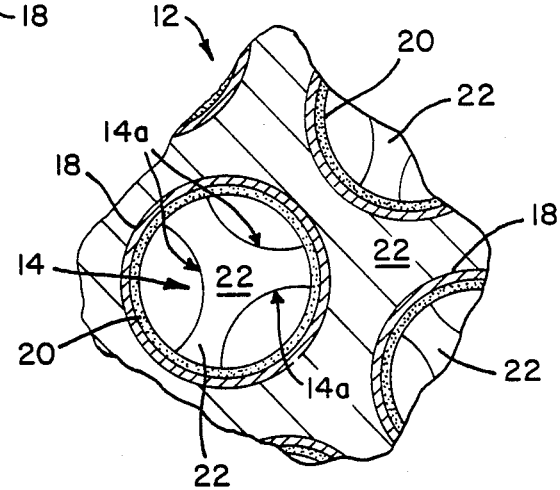
FIG. 2 shows a cutaway view of an enlarged detail of the electrode of FIG. 1.

FIG. 2 shows a cutaway view of an enlarged detail of the electrode 10. The sintered tantalum body 12 has an irregular surface 22 that surrounds and defines the pores 14 and 14a, for instance. The pore 14 interconnects with pores 14a to form a passage for fluid through the body 12.

The pores 14 are shown with the same size and with round cross-sections for simplicity. However, these pores have irregular sizes and shapes. The size and shape of the pore 14 varies with the size and shape of a powder, and with heat and pressure applied to the powder, such as tantalum, in sintering and forming the electrode.

The passivating layer 18 covers each fiber 22 throughout the body 12. The passivating layer 18 in a preferred version is $Ta_2O_5$. This layer is an oxide that has reactive groups for use in chemical derivatization.

The biochemically active layer 20 covers the passivating layer 18 the surface 22 throughout the body 12. Specifically, a biochemically active layer 20 is wicked into the body 12 and is embedded into the pores 14 and 14a, over the passivating layer 18. Thus, the biochemically active layer 20 covers the entire surface of the electrode body 12, including the external surface of the body 12 and the surfaces of each pore 14 and 14a. In one embodiment the passivating layer 18 is silanized to form a binding agent for the biochemically active layer 20 over the entire surface of the electrode 10.

To form one example of this invention, first, the body 12 of an electrode 10 is touched to a 2% solution of 3-aminoproyltriethoxy silane in 95% ethanol. The electrode 10 wicks this amino-silane solution into its body 12 through the interconnected pores 14 and 14a. Next, the electrode 10 is immersed in the amino-silane solution, which is then sonicated to burst and force any residual air bubbles from the pores 14 and 14a. Then the electrode 10 is removed from the amino-silane solution and excess solution is blotted from the body 12. Next, the electrode 10 is kept dry to cure amino-silane on and within the body 12 of the electrode 10. Finally, a receptor molecule is immobilized onto the amino-silane to form part of the biochemically active layer 20.

This receptor molecule could be a hemisuccinate of a hapten that is wicked through the pores 14 of the electrode 10 and is immobilized onto the amino-silane. A carboxyl group of the hapten is connected by a peptide bond to an amino group of the aminosilane embedded on and within the electrode 10. The receptor molecule could also be a protein or amino acid that has an available carboxyl group.

Figure 3:
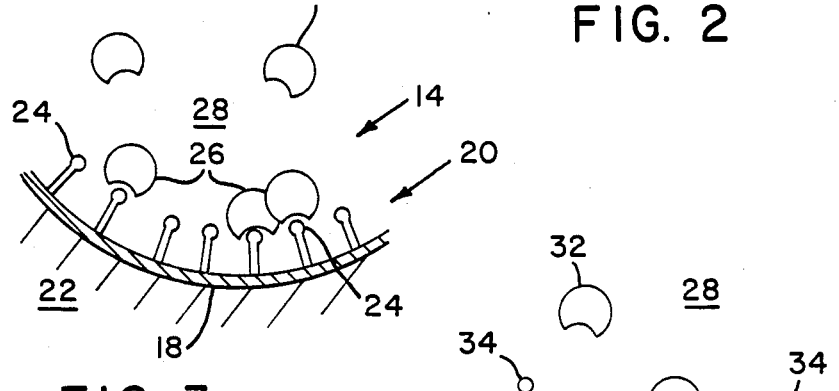
FIG. 3 shows direct binding of molecules to the electrode of FIG. 1.

FIG. 3 shows the direct binding of molecules to the electrode 10 in an enlarged detail of FIG. 2. The passivating layer 18 covers the surface 22. The biochemically active layer 20 covers the passivating layer 18.

The biochemically active layer 20 comprises molecular receptors 24, like hemisuccinate of a hapten, that extend about 100 Angstroms from the passivating layer 18 on the surfaces of the pore 14, for instance. The molecular receptors 24 are immobilized over the passivating layer 18 and are biospecific to analyte molecules 26 that diffuse through a solvent 28 and bind to the molecular receptors 24. Thus, these molecular receptors 24 form a layer that is biochemically active.

The analyte molecules 26 are relatively large and have low dielectric constants. These analyte molecules 26 displace molecules of the solvent 28, which are smaller and have a high dielectric constant, as the analyte molecules 30 bind to the receptor molecules 24.

This changes dielectric properties along the surface 22 of the pores 14, which drastically affects electrical properties of the electrode 10 of FIG. 1, for instance. Thus, electrical properties of the electrode 10 vary with the concentration of analyte molecules 26 in the solvent 28.

In another version, the molecular receptors 24 comprise antibodies bound on the passivating layer 18 and the analyte molecules 26 comprise bacteria, for instance. Such bacteria have haptens and bind through their haptens to the antibodies, which are bound on the passivating layer 18.

In another version, the receptor molecules 24 comprise antigens and the analyte molecules 30 comprise biospecific antibodies. The molecular receptors 24 extend substantially at right angles to any of the surfaces in the electrode 10, which are covered by the passivating layer 18.

Other receptor molecules can comprise the biochemically active layer 20 to which biospecific analyte molecules bind. The chart below lists examples of receptor and analyte molecules that are biospecific to and, therefore, bind to one another.

| Receptors | Analytes |
| --- | --- |
| Antigen | Antibody |
| Hapten | Antibody |
| Enzyme | Substrate Chemical |
| Lectin | Carbohydrate |
| Hormone | Hormone Receptor |
| Hormone | Binding Globulin |
| Neuroreceptor | Neurotransmitter |
| DNA | RNA |
| DNA | DNA |
| RNA | RNA |

In another version, those molecules listed above as analytes can be bound as molecules of a biochemically active layer and those molecules listed above as receptors can be free molecules in a solvent. For instance, when an antibody is bound as a biochemcially active layer, a biospecific antigen will diffuse through a solvent and bind onto that antibody. Examples of biospecific receptor and analyte molecules are discussed in the Newman Patent Application.

Figure 4:
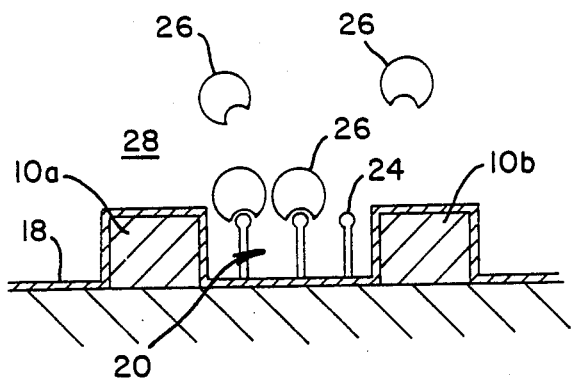
FIG. 4 shows direct binding of molecules in a capacitive affinity sensor.

FIG. 4 schematically shows a cutaway view of a capacitive affinity sensor. The biochemically active layer 20 between two electrodes 10a and 10b forms a dielectric material of the capacitive affinity sensor. Capacitance between the electrodes 10a and 10b changes as analyte molecules 26 bind to the receptor molecules 24 of the biochemically active layer 20. The Newman Patent Application describes a direct binding embodiment of a capacitive affinity sensor having a biochemical layer between two electrodes.

Large analyte molecules 26 are preferred in direct binding versions of the invention, as shown in FIGS. 3 and 4. Such analyte molecules are larger than 150,000 daltons and include bacteria, viruses, other antibodies, or protein. The larger the analyte molecule 26 and the lower its dielectric properties, the greater the change in the dielectric properties of an electrode as the analyte molecules 26 displace high dielectric solvent 28 and bind to the receptor molecules 24.

The receptor molecules 30 comprise antibodies in another version. The following chart lists examples antibodies used as receptor molecules 30 and biospecific analytes that directly bind to these bound antibodies.

| Receptor Molecules | Analyte |
| --- | --- |
| bio-specific antibody | bacteria |
| bio-specific antibody | viruses |
| bio-specific antibody | a second antibody |
| bio-specific antibody | large molecule analytes such as protein molecules |

Figure 5:
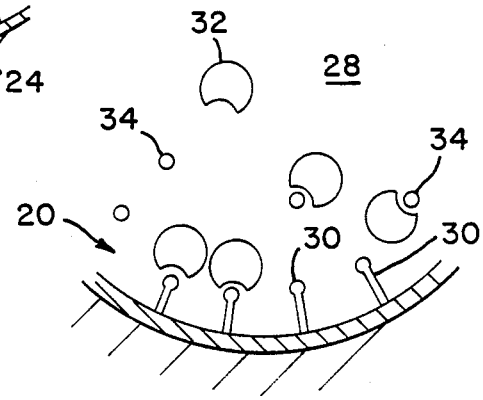
FIG. 5 shows competitive binding of molecules to the electrode of FIG. 1.

FIG. 5 shows the competitive binding of molecules to the electrode 10 in an enlarged detail of FIG. 2. The passivating layer 18 covers the surface 22. The biochemically active layer 20 covers the passivating layer 18.

The biochemically active layer 20 comprises molecular receptors like a hapten 30, which are bound to extend about 100 Angstroms above the passivating layer 18. An antibody 32 is biospecific to and binds to the hapten 30. Thus, these haptens form a biochemically active layer 20.

A free analyte 34 is introduced into and diffuses through the solvent 28. The antibodies 32 are biospecific, not only to the hapten 30, but also to the analyte 34. Thus, the hapten 30 and the analyte 34 compete to bind with an antibody 32. The antibodies 32 are displaced from the hapten 30 by the analyte 34. The antibodies 32 diffuse through the solvent 28, away from the surface of a pore 14, to bind with the free analyte 34. The amount of antibodies 32, which diffuse through the solvent 28 from the hapten 30, is proportional to the concentration of the free analyte 34 in the solvent 28.

Figure 6:
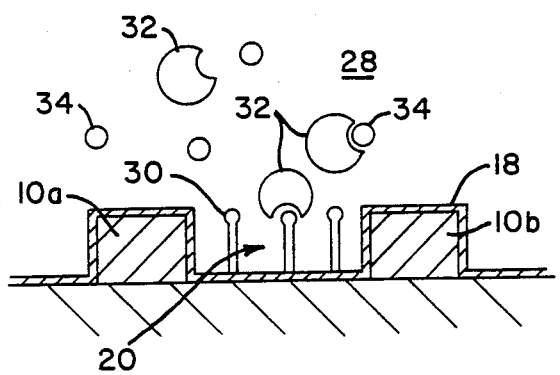
FIG. 6 shows competitive binding of molecules in a capacitive affinity sensor.

Small analyte molecules 34 are preferred in competitive binding versions of the invention, as shown in FIGS. 5 and 6. Such analyte molecules are smaller than 150,000 daltons. A large volume of high dielectric constant solvent 28 replaces the low dielectric constant antibodies 32 that diffuse from the surface of the pore 14. In this way, the dielectric properties and, thus, the electrical properties of an electrode change greatly in proportion to the concentration of free analyte 34 in the solution 28, for instance.

The chart below lists examples of receptor molecules 30 and bound, biospecific molecules 32 that competitively bind to particular analytes.

| Receptor Molecule | Bound Molecule | Particular Analyte |
| --- | --- | --- |
| antigen | antibody | antigen |
| hapten | antibody | hapten |
| polysaccharides | lectin | polysaccharides |
| glycoproteins | lectin | glycoproteins |
| glycolipids | lectin | glycolipids |
| enzyme inhibitor | enzyme | enzyme inhibitor |
| enzyme substrate | enzyme | enzyme substrate |
| enzyme inhibitor | enzyme | enzyme substrate |

FIG. 6 schematically shows a cutaway view of a capacitive affinity sensor. The biochemically active layer 20 between two electrodes 10a and 10b forms a dielectric material of the capacitive affinity sensor. Capacitance between the electrodes 10a and 10b changes as antibodies 32 are displaced from the hapten 30 of the biochemically active layer 20 by the presence of the free analyte 34. The Newman Patent Application describes a competitive binding embodiment of a capacitive affinity sensor having a biochemical layer between two electrodes.

Figure 7:
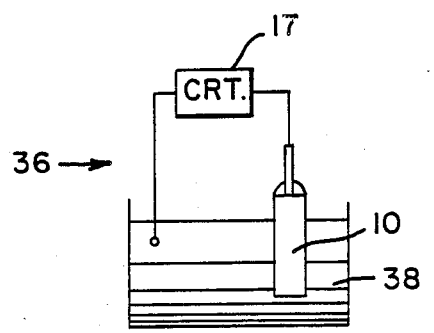
FIG. 7 shows a capacitor with an electrode according to this invention.

FIG. 7 shows a capacitor 36. The electrode 10 is immersed in a fluid 38. The circuit 17 of FIG. 1 connects to the electrode 10 and has a lead that extends into the fluid 38, for instance. The circuit 17 can partially comprise an alternating voltage source that provides a voltage difference between the electrode 10 and the fluid 38. This capacitor 36 has a biochemically active layer embedded in pores of the electrode 10. This layer and these pores are similar to those shown in FIGS. 1–5, for instance. Such a biochemically active layer comprises part of the dielectric material of the capacitor 36. Dielectric properties of the capacitor 36 change as molecules bind to or are displaced from the biochemically active layer comprising the dielectric material.

The amino-silane solution can be applied to the electrode 10 by gas phase reflux techniques. "Covalently Attached Organic Monolayers On Semiconductor Surfaces", by Haller, Journal of the American Chemical Society, Vol. 100, No. 26, 1978, p. 8054, describes a reflux technigue in applying aminopropylsilane to a substrate.

The electrode 10 of FIG. 1 can be used in capacitive chemical sensors to detect hydrocarbons or ions in a liquid.

The electrode 10 of FIG. 1 can be a microcolumn, such as an affinity chromotography column. Analyte molecules in a solvent passing through the column bind to the biochemically active layer 20, affecting electrical properties of the electrode 10. A change in the electrical properties of the electrode 10 indicates the presence of analyte molecules in the solvent.

Also, the electrode 10 can be a filter to charged molecules. An electrical field of the electrode 10 can attract charged and polar molecules, and can pass uncharged and non-polar molecules through the interconnected pores 14 of the electrode 10.

According to this invention, an electrode has a porous body and a biochemically active layer embedded in pores that interconnect through the body. Analyte molecules bind to or displace other molecules from the biochemically active layer to drastically affect the dielectric properties of the electrode, and thus, its electrical properties.

What is claimed is:

1. An apparatus comprising:
   an electrode having a body with pores that interconnect;
   a passivating layer over the body; and
   a biochemically active layer immobilized on the passivating layer and embedded in the pores of the body.

2. The apparatus of claim 1, the biochemically active layer comprising receptor molecules extending from a surface of the pores.

3. The apparatus of claim 2, the body comprising a sintered material.

4. The apparatus of claim 2, the receptor molecules comprising a means for directly binding with analyte molecules.

5. The apparatus of claim 4, the electrode comprising one electrode of a capacitive affinity sensor, and the biochemically active layer comprising a dielectric material of the capacitive affinity sensor.

6. The apparatus of claim 2, the biochemically active layer also comprising a means for competitively binding with the receptor molecules and an analyte molecule.

7. The apparatus of claim 6, the electrode comprising one electrode of a capacitive affinity sensor, and the biochemically active layer comprising a dielectric material of the capacitive affinity sensor.

8. A method comprising:
   applying a passivating layer over an electrode having pores that connect through the electrode;
   immobilizing a biochemically active layer on the passivating layer and embedding the biochemically active layer into the pores of the electrode;
   introducing into the pores of the electrode a fluid having analyte molecules that are biospecific to the biochemically active layer and which biochemically affect the biochemically active layer; and
   determining a change in electrical properties of the electrode as the analyte molecules affect the biochemically active layer.

9. The method of claim 8 comprising immobilizing a receptor molecule on the passivating layer as part of the biochemically active layer.

10. The method of claim 9 comprising relating electrical conductivity of the electrode to a concentration of analyte molecules in the fluid.

11. The method of claim 10 comprising sintering a material to form the electrode.

12. The method of claim 11 comprising forming the biochemically active layer with molecules that bind directly with the analyte molecules.

13. The method of claim 11 comprising forming the biochemically active layer with molecules that bind competitively with the analyte molecules.

* * * * *